United States Patent [19]

Montagnier et al.

[11] Patent Number: 5,217,861

[45] Date of Patent: Jun. 8, 1993

[54] ANTIGEN OF A HUMAN RETROUIRUS, NAMELY P18 PROTEIN OF HUMAN IMMUNODEFICIENCY VIRUS (HIV), COMPOSITIONS CONTAINING THE ANTIGEN, A DIAGNOSTIC METHOD FOR DETECTING ACQUIRED IMMUNE DEFICIENCY SYNDROME (AIDS) AND PRE-AIDS AND A KIT THEREFOR

[75] Inventors: Luc Montagnier, Le Plessis-Robinson; Jean-Claude Chermann, Elancourt; Barre-Sinoussi, Issy Les Moulineaux; Francoise Vezinet-Brun, Paris; Christine Rouzioux, Paris; Willy Rozenbaum, Paris; Charles Dauguet, Paris; Jacqueline Gruest, L'Hay Les Roses; Marie-Theresa Nugeyre, Paris; Francoise Rey, Paris; Claudine Axler-Blin, Paris; Solange Chamaret, Paris, all of France

[73] Assignee: Institut Pasteur, France

[21] Appl. No.: 158,073

[22] Filed: Feb. 12, 1988

Related U.S. Application Data

[63] Continuation of Ser. No. 914,156, Oct. 1, 1986, abandoned, which is a continuation of Ser. No. 706,562, Feb. 22, 1985, abandoned, which is a continuation-in-part of Ser. No. 558,109, Dec. 5, 1983, abandoned.

[30] Foreign Application Priority Data

Sep. 15, 1983 [GB] United Kingdom ................. 8324800
Sep. 16, 1984 [ZA] South Africa ....................... 84/7005

[51] Int. Cl.$^5$ ........................................... G01N 33/569
[52] U.S. Cl. ........................................ 435/5; 435/7.1; 435/7.92; 435/7.93; 435/7.94; 435/7.95; 435/974; 530/350; 930/221
[58] Field of Search ............... 435/517, 29, 259, 800, 435/235-239, 188, 7.1, 7.92-7.95, 974; 530/350; 930/221

[56] References Cited

U.S. PATENT DOCUMENTS

| | | | |
|---|---|---|---|
| 4,520,113 | 5/1985 | Gallo | 436/504 |
| 4,629,783 | 12/1986 | Cosand | 530/324 |
| 4,751,180 | 6/1988 | Cousens et al. | 435/68 |
| 4,784,941 | 11/1988 | Watanabe et al. | 435/5 |
| 4,843,011 | 6/1989 | Sarngadharan et al. | 435/240.27 |

FOREIGN PATENT DOCUMENTS

| | | | |
|---|---|---|---|
| 138667 | 4/1985 | European Pat. Off. | 435/5 |
| 3636540 | 10/1986 | Fed. Rep. of Germany | 435/5 |
| WO86/04336 | 7/1986 | World Int. Prop. O. | 435/5 |

OTHER PUBLICATIONS

Barre-Sinoussi et al., "Analysis and Immunological Properties of Lymphadenopathy Associated Virus (LAV) Structural Proteins", Retroviruses Hum. Pathol. Int. Symp. Meeting Date 1984, 343-51.

Ferns et al., "Characterization of Monoclonal Antibodies Against the Human Immunodificiency Virus (HIV) gag Products and Their Use in Monitoring HIV Isolate Variation", 9 Gen. Virol., 68 (1987) 1543-51.

Krause et al., "Isolation of human immunodeficiency virus-related simian immunodeficiency viruses from African green monkeys", Proc. Natl. Acad. Sci. USA, 86 (1989) 2892-6.

Chassagne et al., "A Monoclonal Antibody Against LAV GAG Precursor: Use for Viral Protein Analysis and Analysis and Antigenic Expression in Infected Cells", J. Immunol. 136(1986) 1442-5.

(List continued on next page.)

*Primary Examiner*—Christine Nucker
*Attorney, Agent, or Firm*—Finnegan, Henderson, Farabow, Garrett & Dunner

[57] ABSTRACT

Protein compositions containing proteins of the lymphadenopathy virus, which compositions are used for diagnosis of antibodies of such protein in biological fluids, especially blood serum, for the detection or absence of infection. Such compositions contain typically the p18, p13 and/or p25 proteins.

11 Claims, 5 Drawing Sheets

OTHER PUBLICATIONS

Van de Perre et al., "Detection of p17 antigen in lymphocytes but not epithelial cells from cervicovaginal secretions of women seropositive for HIV: implications for heterosexual transmission of the virus", Genitourin Med., 64 (1988) 30-33.

L. Montagnier et al., "A New Type of Retrovirus Isolated From Patients Presenting With Lymphadenopathy and Acquired Immune Deficiency: Structural and Antigenic Relatedness with Equine Infectious Anaemia Virus", Ann. Virol. (Inst. Pasteur) 1984, 135 E, 119-134.

Barré-Sinoussi, F. et al., Science 220:868-871 (May 1983).

Montagnier, L. et al., *Human T-cell Leukemia Lymphoma Viruses*, Cold Spring Harbor, N.Y., Gallo R. C. et al., eds (1984), pp. 363-379, Oral presentation Sep. 14-16, 1983.

Norman, C., Science 230:640-643 (Nov. 1985).

Montagnier, L. et al., Science 225:63-66 (Jul. 1984).

Wain-Hobson, S. et al., Cell, 40:9-17 (Jan. 1985).

Montagnier, L. et al., Virology 144:283-289 (1985).

1 2 3 4 5 6 7 8 9 10

93-
69-
46-

30-

15-

ANTIGEN OF A HUMAN RETROUIRUS, NAMELY P18 PROTEIN OF HUMAN IMMUNODEFICIENCY VIRUS (HIV), COMPOSITIONS CONTAINING THE ANTIGEN, A DIAGNOSTIC METHOD FOR DETECTING ACQUIRED IMMUNE DEFICIENCY SYNDROME (AIDS) AND PRE-AIDS AND A KIT THEREFOR

CROSS-REFERENCE TO RELATED APPLICATIONS

This application is a continuation of application Ser. No. 914,156, filed Oct. 1, 1986, now abandoned which is a continuation of application Ser. No. 706,562, filed Feb. 22, 1985, now abandoned, which is a continuation-in-part of application Ser. No. 558,109, filed Dec. 5, 1983, now abandoned, which are incorporated by reference herein.

BACKGROUND OF THE INVENTION

1. Field of the Invention

The acquired immune deficiency syndrome (AIDS) has recently been recognized in several countries. The disease has been reported mainly in homosexual males with multiple partners, and epidemiological studies suggest horizontal transmission by sexual routes as well as by intravenous drug administration and blood transfusion. The pronounced depression of cellular immunity that occurs in patients with AIDS and the quantitative modification of subpopulations of their T-lymphocytes suggest that T-cells or a subset of T-cells might be a preferential target for the putative infectious agent. Alternatively, these modifications could result from subsequent infections. The depressed cellular immunity may result in serious opportunistic infections in AIDS patients, many of whom also develop Kaposi's sarcoma. However, a picture of persistent multiple lymphadenopathies has also been described in homosexual males and infants who may or may not go on the to develop AIDS. The histological aspect of such lymph nodes is that of reactive hyperplasia. Such cases may correspond to a prodromal form or to a milder form of the disease.

In view of similarities in tropism to the recently discovered human T-cell leukemia/lymphoma virus (HTLV-I), these were initial suggestions that it was this virus which was the etiologic agent of lymphadenopathy syndrome (LAS) or acquired patients which reacted with HTLV-I proteins. However, the many differences between patients having LAS or AIDS and those individuals who had been infected with HTLV-I suggested that the agents might be different. Particularly, the etiologic agent associated with LAS or AIDS was cytotoxic to the T-helper subset of T-cells, while infection with HTLV-I resulted in transformation rather than cell death. The fact that the etiologic agent was cytotoxic and tropic for T-cells created substantial difficulties in identifying and isolating the etiologic agent.

Publications of Interest

Illustrative of the many articles concerning retroviruses associated with LAS or AIDS are Guroff et al; *J. Exp. Med.* 154:1957-64 (1981), Gallo et al.; *J. Natl. Cancer Inst.*, 69, (No. 6) p. 1209 (1982), Poiesz et al., Proc. Natl. Acad. Sci. U.S.A. 77:7415-19, p. 7415 (1980), Barre-Sinoussi et al., Ann, Microbiol (Institut Pasteur), 130B, 349, (1979), Galman et al., Science (1983), 220:862 and Gallo et al., (1983), 220:865, Kalyanaraman et al., Ibid. (1982) 218:571, Gallo et al., *Science* (1983) 220:865-867; Barre-Sinoussi et al., Science (1983) 220:868-870; Rey et al., *Bio. Chem. Bio. Phys. Res. Comm.* (1984) 121:126-133; Ellrodt et al., *Lancet* (1984) 1383-1385; Gajdusck, *Lancet* (1984) 1415-1416; Kalyanaraman et al., *Science* (1984) 225:321-323; Chermann et al., *Antibot, Chemother.* (1984) 32: 48-53; Montagnier et al., *Science* (1984) 225:63-66. See also, Shaw et al., *Science* (1984) 226:1165-1171 and references cited therein for a survey of the field. Note also Montagnier et al., Ann. Virol (Institut Pasteur), 135E, p. 119-134, No. 1 (1984) which is specifically incorporated herein by reference, and the references cited therein.

With the lymphadenopathy syndrom (LAS) or acquired immune deficiency syndrome (AIDS) becoming a major health threat, substantial efforts have been made to determine the cause of the disease. It has therefore become a major effort to find ways to screen blood to detect whether the donor may have been infected with the pathogenic cause of the disease.

Methods and compositions are provided for detecting the presence of a retrovirus associated with lymphadenopathy syndrome and/or acquired immune deficiency syndrome. The compositions may be derived, either directly or indirectly, from the retrovirus. The proteins may be used as reagents for detection of the presence of antibodies in human blood as indicative of a prior or existent infection with the retrovirus, as immunogens for the production of antibodies for detection of proteins associated with the retrovirus, or as vaccines. The absence of a reaction is indicative of a negative diagnosis.

The acquired immune deficiency syndrome (AIDS) has recently been recognized in several countries. The disease has been reported mainly in homosexual males with multiple partners, and epidemiological studies suggest horizontal transmission by sexual routes as well as by intravenous drug administration and blood transfusion. The pronounced depression of cellular immunity that occurs in patients with AIDS and the quantitative modifications of subpopulations of their T lymphocytes suggest that T cells or a subset of T cells might be a preferential target for the putative infectious agent. Alternatively, these modifications may result from subsequent infections. The depressed cellular immunity may result in serious opportunistic infections in AIDS patients, many of whom develop Kaposi's sarcoma. However, a picture of persistent multiple lymphadenopathies has also been described in homosexual males and infants who may or may not develop AIDS. The histological aspect of such lymph nodes is that of reactive hyperplasia. Such cases may correspond to an early or a milder form of the disease.

It has been found that one of the major etiological agents of AIDS and of lymphadenopathy syndrome (LAS), which is often considered as a prodromic sign of AIDS, consists of a T-lymphotropic retrovirus which has been isolated from a lymph node of a homosexual patient with multiple lymphadenopathies. The virus is distinct from the human T-cell leukemia virus (HTLV) family (R. C. Gallo and M. S. Reitz, J. Natl. Cancer Inst., 69 (No. 6), 1209 (1982)). The last mentioned virus has been known as belonging to the so-called HTLV-1 subgroup. The virus of this invention is also distinct from the retrovirus referred to as HTLV-II (Kalyanaraman et al. Science 218:571-3 (1982) mentioned above).

The patient was a 33-year-old homosexual male who sought medical consultation in December 1982 for cervical lymphadenopathy and asthenia (patient 1). Examination showed axillary and inguinal lymphadenopathies. Neither fever nor recent loss of weight were noted. The patient had a history of several episodes of gonorrhea and had been treated for syphilis in September 1982. During interviews he indicated that he had had more than 50 sexual partners per year and had traveled to many countries, including North Africa, Greece, and India. His last trip to New York was in 1979.

Laboratory tests indicated positive serology (immunoglobulin G) for cytomegalovirus (CMV) and Epstein-Barr virus. Herpes simplex virus was detected in cells from his throat that were cultured on human and monkey cells. A biopsy of a cervical lymph node was performed. One sample served for histological examination, which revealed follicular hyperplasia without change of the general structure of the lymph node. Immunohistological studies revealed, in paracortical areas, numerous T lymphocytes (OKT3+). Typing of the whole cellular suspension indicated that 62 percent of the cells were T lymphocytes (OKT3+), 44 percent of the cells were T-helper cells (OKT4+), and 16 percent were suppressor cells (OKT8+).

Cells of the same biopsed lymph node were put in culture medium with phytohemagglutinin (PHA), T-cell growth factor (TCGF), and antiserum to human α-interferon. ("The cells were grown in RPMI-1640 medium supplemented with antibiotics, $10^{-5}$M B-mercaptoethanol, 10 percent fetal calf serum, 0.1 percent sheep antibody to human interferon (neutralizing titer, 7 IU at $10^{-5}$ dilution and 10 percent TCGF, free of PHA")). The reason for using the antiserum to α-interferon was to neutralize endogenous interferon which is secreted by cells chronically infected by viruses, including retroviruses. In the mouse system, it had previously been shown that anti-serum to interferon could increase retrovirus production by a factor of 10 to 50 (F. Barre-Sinoussi et al., Ann. Microbiol. (Institut Pastuer) 130B, 349 (1979). After 3 days, the culture was continued in the same medium without PHA. Samples were regularly taken for reverse transcriptase assay and for examination in the electron microscope.

After 15 days of culture, a reverse transcriptase activity was detected in the culture supernatant by using the ionic conditions described for HTLV-I (Poiesz et al. Proc. Natl. Acad, Sci. U.S.A. 77:7415 (1980)). Virus production continued for 15 days and decreased thereafter, in parallel with the decline of lymphocyte proliferation. Peripheral blood lymphocytes cultured in the same way were consistently negative for reverse transcriptase activity, even after 6 weeks. Cytomegalovirus could be detected, upon prolonged cocultivation with MRC 5 cells, in the original biopsy tissue, but not in the cultured T lymphocytes at any time of the culture.

SUMMARY OF THE INVENTION

The invention relates to the newly isolated virus as a source of the above said antigen which will be defined later.

The subject matter also includes those viruses which produce the same or similar proteins which substantially completely or completely immunologically cross reactive with p13, p18, and p25 protein, preferably with p18 and/or p25 or immunologically equivalent proteins.

The invention also includes a diagnostic method for the detection of infection in humans more particularly the absence or presence of antibodies to proteins of the lymphadenopathy retrovirus (LAV), especially the p18 and/or the p25 proteins.

The invention relates to the newly isolated virus, which will hereafter be termed as $LAV_1$ and will be initially described hereinafter.

DETAILED DESCRIPTION

Figure 1:
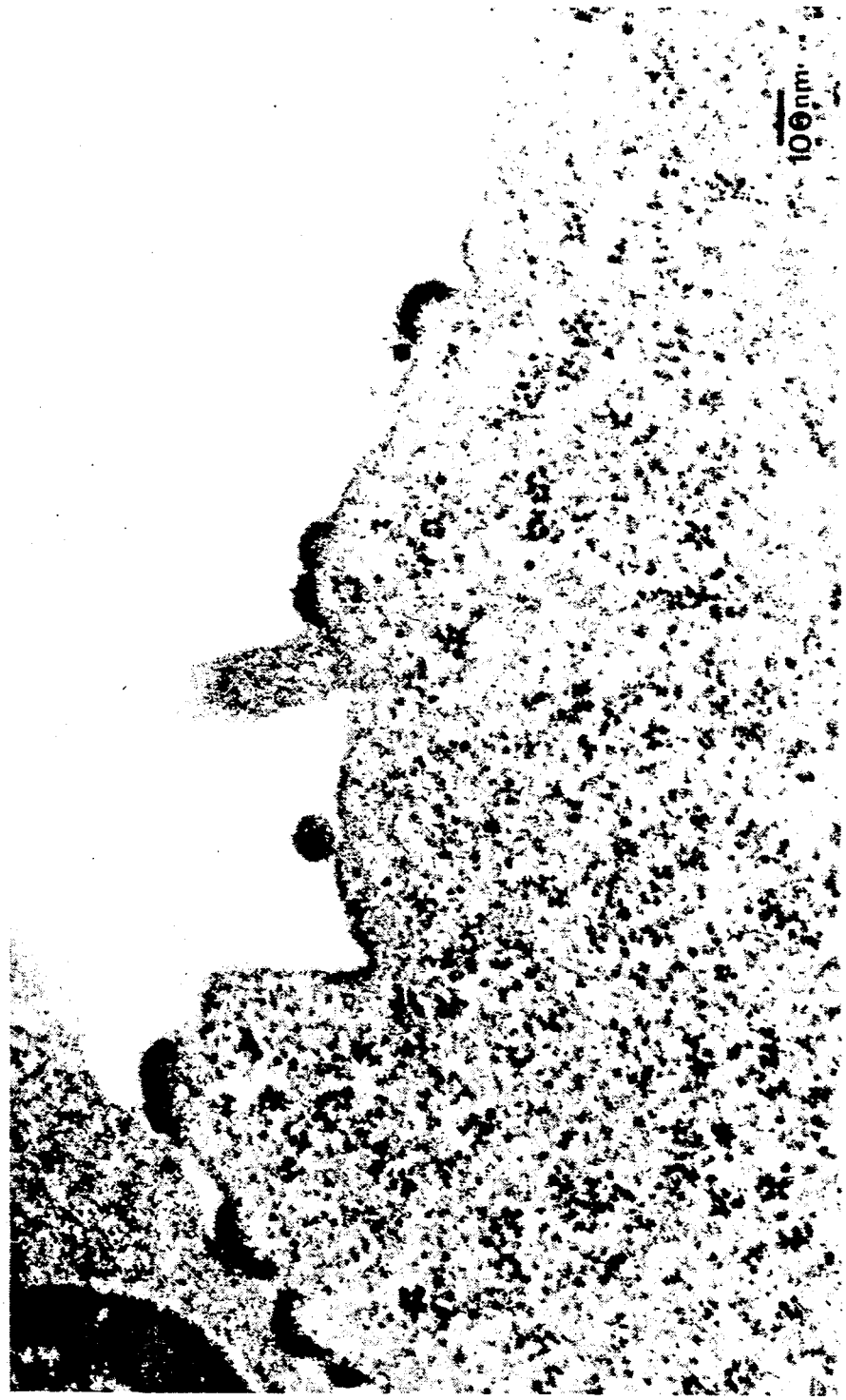
FIG. 1 is an electron micrograph of ultrathin sections of lymphocytes of a healthy adult donor infected with the retrovirus isolated from a haemophiliac patient with AIDS (IDAV2).
Figure 2A:
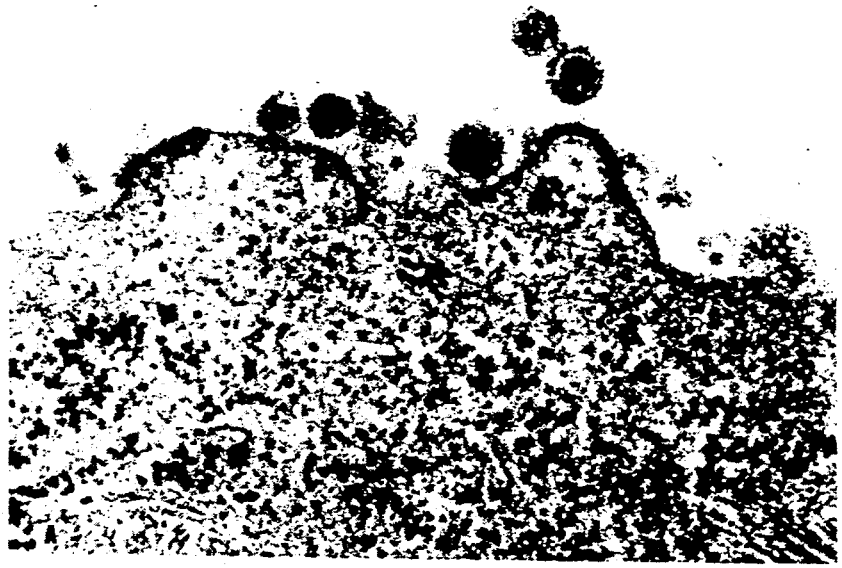
FIG. 2A and 2B is an ultrastructural comparison between HTLV and LAV.
Figure 2B:
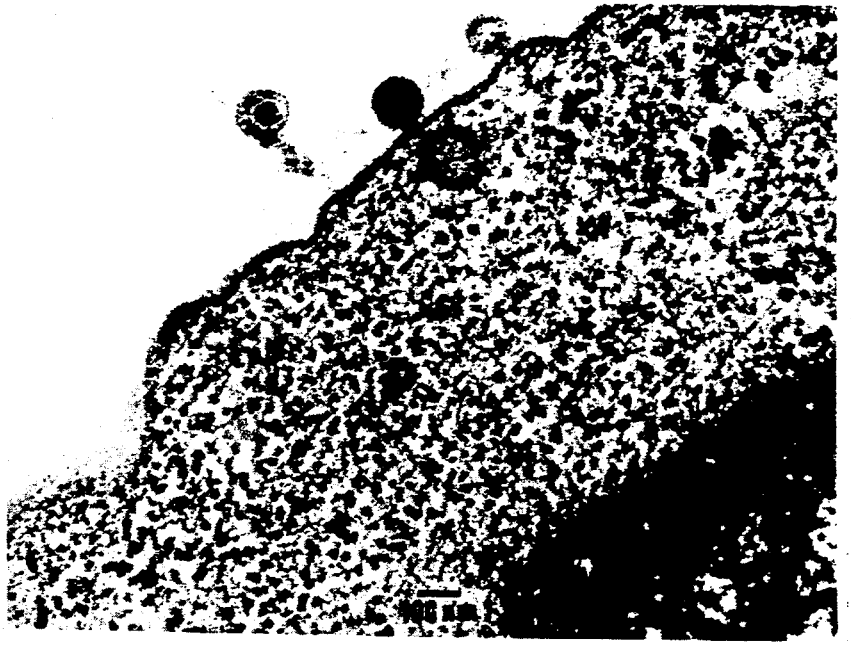
Figure 3:
FIG. 3 is an intracellular vesicle in LAV-infected lymphocytes.
Figures 4A, 5:
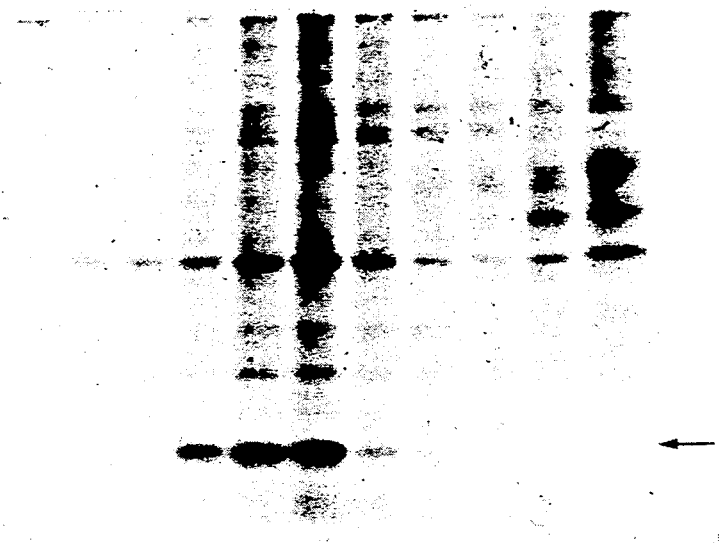
FIG. 4A and 4B is an electrophoresis and autoradiogram of methionine-labelled LAV.
FIG. 5 is a polyacrylamide (12.5%) electrophoresis gel of immunecomplexes between $^{35}$S-labelled virus and horse sera.
Figure 4B:
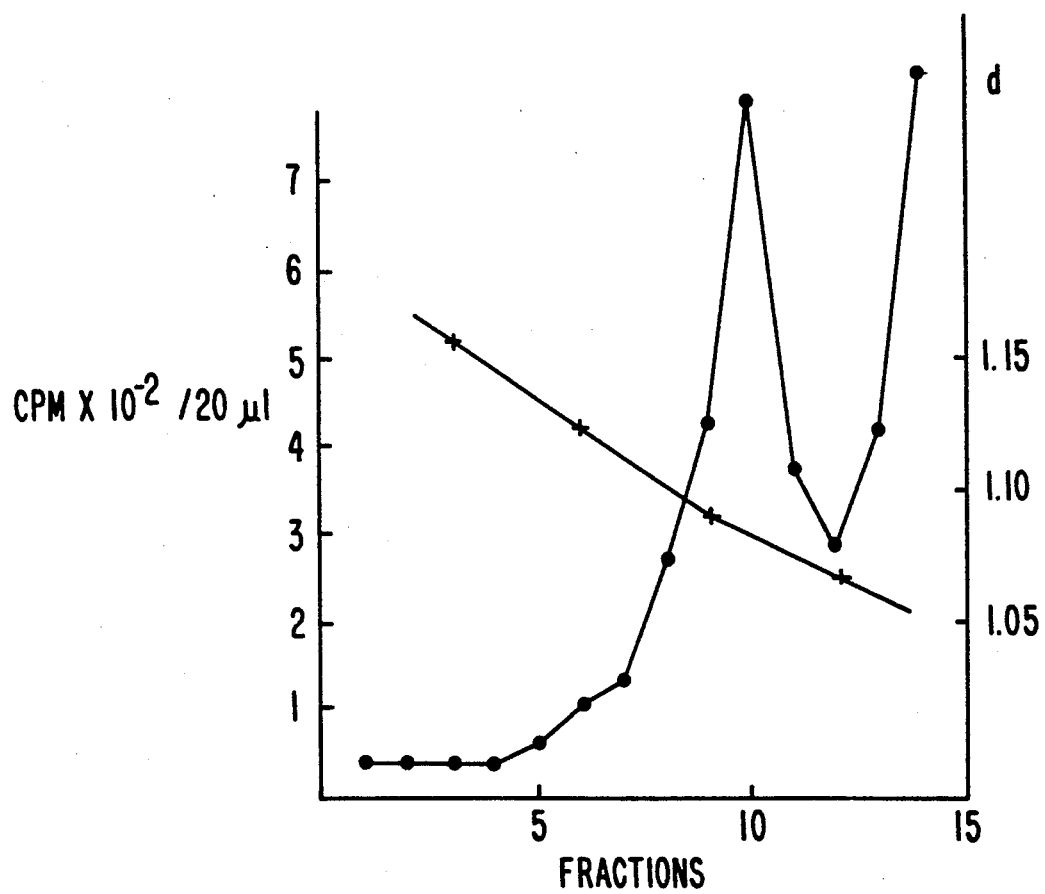

The virus is transmissible to cultures of T lymphocytes obtained from healthy donors. Particularly, virus transmission was attempted with the use of a culture of T lymphocytes established from an adult healthy donor of the Blood Transfusion Center at the Pastuer Institut. On day 3, half of the culture was cocultivated with lymphocytes from the biopsy after centrifugation of the mixed cell suspensions. Reverse transcriptase activity could be detected in the supernatant on day 15 of the co-culture but was not detectable on days 5 and 10. The reverse transcriptase had the same characteristics as that released by the patient's cells and the amount released remained stable for 15 to 20 days. Cells of the uninfected culture of the donor lymphocytes did not release reverse transcriptase activity during this period or up to 6 weeks when the culture was discontinued.

The cell-free supernatant of the infected co-culture was used to infect 3-day-old cultures of T lymphocytes from two umbilical cords, LC1 and LC5, in the presence of Polybrene (2 ug/ml). After a lag period of 7 days, a relatively high titer of reverse transcriptase activity was detected in the supernatant of both cord lymphocyte cultures. Identical cultures, which had not been infected, remained negative. These two successive infections clearly showed that the virus could be progated on normal lymphocytes from either new-borns or adults.

In the above co-cultures one used either the cells of patient 1 as such (they declined and no longer grew) or cells which had been pre-X-rayed or mitomycin C-treated.

The $LAV_1$ virus, or $LAV_1$ virus suspensions, which can be obtained from infected cultures of lymphocytes have characteristics which distinguish them completely from other HTLV. These characteristics will be referred to hereafter and, when appropriate, in relation to the drawing. It shows curves representative of variation of reverse transcriptase activity and [$P^3$H]uridine activity respectively versus successive fractions of the $LAV_1$ virus in the sucrose gradient, after ultracentrifugation therein of the virus contents of a cell-free supernatant obtained from a culture of infected lymphocytes.

The analysis of $LAV_1$ virus by resorting to reverse transcriptase activity can be carried out according to the procedure which was used in relation to virus from patient 1, in FIG. 1. The results of the analysis are illustrated on FIG. 1 described by Barre-Sinoussi et al. 220:868–70 (1983) in the paper Science. Cord blood T lymphocytes infected with virus from patient 1 were labelled for 18 hours with [$^3$H]uridine (28 Ci/mmole, Amersham; 20 uCi/ml). Cell-free supernatant was ultracentrifuged for 1 hour at 50,000 rev/min. The pellet was resuspended in 200 ul of NTE buffer (10 mM tris, pH 7.4, 100 mM NaCl, and 1 mM EDTA) and was centrifuged over a 3-ml linear sucrose gradient (10 to 60 percent) at 55,000 rev/min for 90 minutes in an IEC type SB 498 rotor. Fractions (200 ul) were collected, and 30 1 samples of each fraction were assayed for DNA RNA dependent polymerase activity with 5 mM $Mg^{2+}$ and poly(A)-oligo-(dt)$_{12-18}$ as template primer; a 20-ul portion of each fraction was precipitated with 10 percent trichloroacetic acid and then filtered on a 0.45- m Millipore filter. The $^3$H-labelled acid precipitable material was measured in a Packard B counter.

That the new virus isolate was a retrovirus was further indicated by its density in the above sucrose gradient, which was 1.16, and by its labelling with [$^3$H]uridine (FIG. 1). A fast sedimenting RNA appears to be associated with the $LAV_1$ virus.

Virus-infected cells from the original biopsy as well as infected lymphocytes from the first and second viral passages were used to determine the optimal requirements for reverse transcriptase activity and the template specificity of the enzyme. The results were the same in all instances. The reverse transcriptase activity displayed a strong affinity for polyadenylate-oligodeoxythymidylate) [poly(A)-oligo(dt)$_{12-18}$], and required $Mg^{2+}$ with an optimal concentration (5 mM) and an optimal pH of 7.8. The reaction was not inhibited by actinomycin D. This character, as well as the preferential specificity for riboseadenylate-deoxythymidylate over deoxyadenylate-deoxythymidylate, distinguish the viral enzyme from DNA-dependent polymerases.

Electron microscopy of ultrathin sections of virus-producing cells show two types of particles, presumably corresponding to the immature and mature forms of the virus; immature particles are budding at the cell surface, with a dense crescent in close contact with the plasma membrane. Occasionally, some particles remain in this state, while being freed from the cell surface.

Mature particles have a quite different morphology with a small, dense, eccentric core (mean diameter: 41 nM). Most of virions are round (mean diameter: 139 nM) or ovoid, but in some pictures, especially in the particles seen in the original culture from which the virus was isolated, a tailed morphology can also be observed. The latter form can also be observed in cytoplasmic vesicles which were released in the medium. Such particles are also formed by budding from vesicle membranes.

Morphology of mature particles is clearly distinct from HTLV, whose large core has a mean diameter of 92 nM.

Helper T-lymphocytes (Leu 3 cells) are the main target of the virus. In other words the $LAV_1$ virus has particular tropism for these cells. Leu 3 cells are recognizable by the monoclonal antibodies commercialized by ORTHO under the trademark OKT4. In contrast, enriched cultures of Leu 2 cells, which are mainly suppressor or cytotoxic cells and which are recognized by the monoclonal antibodies commercialized by ORTHO under the trademark OKT8 did not produce, when infected under the same conditions, any detectable RT activity even 6 weeks after virus infection.

In most cases of AIDS, the ratio of OKT4+ over OKT8+ cells which is normally over 1, is depressed to values as low as 0.1 or less.

The $LAV_1$ virus is also immunologically distinct from previously known HTLV-1 isolates from cultured T lymphocytes of patients with T lymphomas and T leukemias. The antibodies used were specific for the p19 and p24 core proteins of HTLV-1. A monoclonal antibody to p19 (M. Robert-Guroff et al. J. Exp. Med. 154:1957–64 (1981)) and a polyclonal goat antibody to p24 Kalyanaraman et al., J. Virol., 38:906–915 (1981)) were used in an indirect fluorescence assay against infected cells from the biopsy of patient 1 and lymphocytes obtained from a healthy donor and infected with the same virus. The $LAV_1$ virus-producing cells did not react with either type of antibody, whereas two lines of cord lymphocytes chronically infected with HTVL 1 (M. Popovic, P. S. Sarin, M. Robert-Guroff, V. S. Kalyanaraman, D. Mann, J. Minowads, R. C. Gallo, Science 219:856–859 (1983)) and used as controls showed strong fluorescence.

In order to determine which viral antigen was recognized by antibodies present in the patient's sera, several immunoprecipitation experiments were carried out. Cord lymphocytes infected with virus from patient 1 and uninfected controls were labelled with [$^{35}$S]methionine for 20 hours. Cells were lysed with detergents, and a cytoplasmic S10 extract was made. Labelled virus released in the supernatant was banded in a sucrose gradient. Both materials were immunoprecipitated by antiserum to HTVL-1 p24, by serum from patient 1, and by serum samples from healthy donors. Immunocomplexes were analyzed by polyacrylamide gel electrophoresis under denaturing conditions. A p25 protein present in the virus-infected cells from patient 1 and in LC1 cells infected with this virus, was specifically recognized by serum from patient 1 but not by antiserum to HTLV-1 p24 obtained under similar conditions or by serum of normal donors. Conversely, the p24 present in control HTLV-infected cell extracts was recognized by antibodies to HTLV but not by serum from patient 1.

The main protein (p25) detected after purification of $^{35}$S-methionine-labelled virus has a molecular weight of about 25,000 (or 25K). This is the only protein detectable under such labelling conditions which is recognized by the serum of patient 1. By analogy with other retroviruses, this major protein was considered to be located in the viral core.

This can be confirmed by immuno-electron microscopy experiments, which show that the patient's serum can agglutinate the viral cores. Conversely, an antiserum raised in rabbit against an ether treated virus did not precipitate the p25 protein.

$^{35}$S-methione could also be incorporated into proteins of higher molecular weight (46K and 70K).

In addition to protein p25, other proteins were detectable upon gel electrophoresis under analogous denaturating conditions when the virus was initially labelled with other radioactively labelled amino acids, i.e. $^{35}$S-cysteine. The proteins which were then detected in addition to p25, have a molecular weight of about 18,000 (p18) and 12,000 "p12", the numbers in the bracketed designations indicating the approximate molecular weight in Kilodaltons. The virus was metabolically labelled with $^{35}$S-cysteine. The same protein bands are likewise visible after silver staining. These proteins are likewise identified in sera of patients suffering from or having LAS or AIDS.

The viral origin of other proteins seen in polyacrylamide gel electrophoresis of purified virus is more difficult to assess. A p15 protein could be seen after silver staining, but was much weaker after $^{35}$S-methionine perhaps due to the paucity of this amino-acid in the protein. In the higher MW range, a contamination of the virus by cellular proteins; either inside or outside the viral envelope, is likely. A 36K and a 42K protein and a 80K protein were constantly found to be associated with the purified virus and may represent the major envelope proteins.

No protein immunologically cross-reactive with the p19 of viruses of the HTLV family has been isolated from LAV$_1$ extracts.

The invention concerns more particularly the extracts of said virus as soon as they can be recognized immunologically by sera of patients afflicted with LAS or AIDS. Needless to say any type of immunological assay may be brought into play. By way of example, immunofluorescence or immunoenzymatic assays or radio-immunoprecipitation tests are particularly suitable.

As soon as the core proteins become exposed to sera of diseased patients, the immunological detection becomes possible. Therefore, the invention concerns all extracts of the virus, whether it be the crudest ones-particularly mere virus lysates-or the more purified ones, particularly extracts enriched in the p25 protein or even the purified p25 protein or a protein immunologically related therewith. In a similar manner, the invention concerns all extracts of the virus whether it be the crudest ones-particularly virus lysates-or more purified ones, which contain the p18 protein, or even the purified p18 protein or any protein or polypeptide immunologically the same, equivalent to or related thereto. The invention concerns proteins or polypeptides (purified or not) as such, free of the extract. The same applies to the p12-p13 protein. Any purification procedure for obtaining any of said proteins may be resorted to. By way of example only, one may use purification procedures such as disclosed by Montelaro et al; J. of Virology, June 1982, pp. 1029-1038. Other methods of course may be used to obtain said proteins or polypeptides immunologically cross-reactive with them, particularly genetic engineering methods, including causing the expression in a suitable host of a DNA sequence encoding such a protein or polypeptide.

Other preferred extracts obtained from the virus contain in addition to other proteins, either protein p12 or protein p18 or both. Preferred extracts may include the three proteins p12, p18, and p25 or p25 with either one or the other of p12 or p18a specially preferred one containing in addition to other proteins, the proteins p12 and p25. Such diagnostic compositions containing one or more of the proteins which immunologically react with the antibodies in the biological fluid of the patient, are useful for determination of the infection or its absence. Compositions containing one or several of said proteins or polypeptides, whatever the sources thereof, or methods for making them, may be substituted for the above said extracts, for the purpose of providing means for determining the presence of AIDS antibodies in a patient.

In respect other than noted above, the composition which contains the p13 and p18 proteins are preferably like compositions which contain the p25 protein, free of the p19 protein which is immunologically related to the p19 protein of the HTLV viruses. The same applies to the preferred compositions which contains the p18, p36, p42 and p80 proteins.

Antibodies to p12, p13, p18, p19, p25, p36, p42 and to p80 proteins have been detected in the sera of lymphadenopathy and AIDS patients, whether the composition contains one or more of the proteins.

The invention concerns more generally extracts of any virus having similar phenotype and immunologically related to that obtained from LAV$_1$ as well as the biologically pure proteins which have been defined here above. Sources of viruses of the LAV type consist of T-lymphocyte cultures isolatable from LAS—and AIDS—patients or from haemophiliacs.

In that respect, other preferred extracts are those obtained from two retroviruses obtained by propagation on normal lymphocytes of the retroviruses isolated from:

1) lymph node lymphocytes of a caucasian homosexual with multiple partners, having extensive Kaposi sarcoma lesions and severe lymphopenia with practically no OKT4+ lymphocytes in his blood;

2) blood lymphocytes of a young G haemophiliac presenting neurotoxoplasmosis and OKT4+/OKT8+ ratio of 0.1.

These two retroviruses have been named IDAV1, and IDAV2 respectively (for Immune Deficiency Associated Virus). Results of partial characterization obtained so far indicate similarity —if not identity—IDAV1 and IDAV2 to LAV1; because of the following:

same ionic requirements and template specificities of reverse transcriptase, same morphology in ultrathin sections, antigenically related p25 proteins: serum of LAV1 patient immunoprecipitates p25 from IDAV1 and IDAV2; conversely, serum from IDAV2 patient immunoprecipitates LAV1 p25.

IDAV1 patient serum seemed to have a lower antibodies titer and gave a weak precipitation band for LAV1 and IDAV1 p25 proteins. The p25 protein of IDAV1 and IDAV2 was not recognized by HTLV p24 antiserum.

These similarities suggest that all these three isolates belong to the same group of viruses.

The invention further relates to a method of in vitro diagnosis of LAS or AIDS, which comprises contacting a serum or other biological medium from a patient to be diagnosed with a virus extract or a composition containing one said protein, e.g. the p18 protein, or several of said proteins, e.g. the p18 and p25 proteins as above defined and detecting the immunological reaction.

Preferred methods bring into play immunoenzymatic or immunofluorescent assays, particularly according to the ELISA technique. Assays may be either direct or indirect immunoenzymatic or immunofluorescent assays.

Thus, the invention also relates to labelled virus extracts or proteins whatever the type of labelling: enzymatic, fluorescent, radioactive, etc..

Such assays include for instance:

depositing determined amounts of the extract according to the invention in the wells of titration microplate;

introducing in said wells increasing dilutions of the serum to be diagnosed;

incubating the microplate;

washing the microplate extensively;

introducing in the wells of the microplate labelled antibodies directed against blood immunoglobulins, the labelling being by an enzyme selected among those which are capable of hydrolysing a substrate, whereby the latter then undergoes a modification of its absorption of radiations, at least in a determined wavelength band, and detecting, preferably in a comparative manner with respect to a control, the amount of substrate hydrolysis as a measure of the potential risks or effective presence of the disease.

The invention also relates to kits for the above-said diagnosis which comprise:

an extract or more purified fraction of the above-said types of viruses, or composition comprising at least one of said proteins, said extract, or fraction or composition being labelled, such as by a radioactive, enzymatic or immunofluorescent label;

human anti-immunoglobulins or protein A (advantageously fixed on a water-insoluble support such as agarose beads);

a lymphocyte extract obtained from a healthy person;

buffers and, if appropriate, substrates for the vizualization of the label.

Other features of the invention will further appear as the description proceeds of preferred isolation and culturing procedures of the relevant virus, of preferred extraction methods, of an extract suitable as diagnostic means, of a preferred diagnosis technique and of the results that can be achieved.

EXPERIMENTAL

The following examples supplement experimental work reported above, and are presented by way of illustration and not by way of limitation.

1. VIRUS PROPAGATION

Cultured T-lymphocytes from either umbilical cord or blood, or also bone marrow cells from healthy, virus negative, adult donors are suitable for virus propagation.

There is, however, some variation from individual to individual in the capacity of lymphocytes to grow the virus. Therefore, it is preferable to select an adult healthy donor, who had no antibodies against the virus and whose lymphocytes repeatedly did not release spontaneously virus, as detected by reverse transcriptase activity (RT) nor expressed viral proteins.

Lymphocytes of the donor were obtained and separated by cytophoresis and stored frozen at $-180°$ C. in liquid nitrogen, in RPMI 1640 medium, supplemented with 50% decomplemented human serum and 10% DMSO until used.

For viral infection, lymphocytes were put in culture (RPME 1640 medium) with phytohaemagglutinin (PHA) at the concentration of $5 \times 10^6$ cells/ml for 3 days.

Then, the medium was removed and cells resuspended in viral suspension (crude supernatant of virus producing lymphocytes, stored at $-80°$ C.). Optimal conditions of cell/virus concentrations were $2 \times 10^6$ cells for 5 to 10,000 cpm of RT activity, the latter determined as previously described. After 24 hours, cells were centrifuged to remove the unadsorbed virus and resuspended in culture PHA-free medium and supplemented with PHA-free TCGF (Interleukin 2): (0.5-1 U/ml, final concentration), POLYBREN (Sigma) 2 ug/ml and anti-interferon sheep serum, inactivated at 56° C. for 30 minutes (0.1% of a serum which is able to neutralize 7 U of leucocyte interferon at a 1/100,000 dilution).

Virus production was tested every 3 days by RT activity determination on 1 ml samples.

The presence of anti-interferon serum is important in virus production: when lymphocytes were infected in the absence of anti-human- -interferon serum, virus production, as assayed by RT activity, was very low or delayed. Since the sheep antiserum used was raised against partly purified-leucocyte interferon, made according to the Cantell technique, the role of components other than interferon cannot be excluded.

Virus production starts usually from day 9 to 15 after infection, and lasts for 10-15 days. In no case was the emergence of a continuous permanent line observed.

2. VIRUS PURIFICATION:

For its use in ELISA, the virus was concentrated by 10% polyethyleneglycol (PEG 6000) precipitation and banded twice to equilibrium in a 20-60% sucrose gradient. The viral band at density 1.16 is then recovered and usable as such for ELISA assays.

For use in an RIPA radioimmune precipitation assay, purification in isotonic gradients of Metrizamide (sold under the trademark NYCODENZ by Nyegaard, Oslo) were found to be preferable. Viral density in such gradients was very low (1.10-1.11).

Metabolic labelling with $^{35}$S-methionine of cells and virus (RIPA) followed by polyacrylamide gel electrophoresis were performed as above described, with the following modifications for RIPA: virus purified in NYCODENZ or sucrose gradient (as described in Science 1983, 220, 868-870) was lysed in 4 volumes of RIPA containing 500 U/ml of aprotinin. Incubation with 5 ul of serum to be tested was made for 1 hour at 37° C. and then 18 hours at +4° C. Further incubation of the immunocomplexes with protein A SEPHAROSE beads was for 3 hours at +4° C.

3. PREPARATION OF THE VIRUS EXTRACT FOR ELISA ASSAYS:

Virus purified in sucrose gradient as above described, is lysed in RIPA buffer (0.5% SDA) and coated on wells of microtest plates (Nunc).

Preferred conditions for the ELISA assay are summed up thereafter.

After addition to duplicate wells of serial dilutions of each serum to be tested, the specifically fixed IgGs are revealed by goat anti-human IgG coupled with peroxidase. The enzymatic reaction is carried out on orthophenylene-diamine as substrate and read with an automatic spectrophotometer at 492 nM.

On the same plate each serum is tested on a control antigen (a crude cytoplasmic lysate of uninfected T-lymphocytes from the same donor) in order to eliminate unspecific binding, which can be high with some sera.

Sera are considered as positive (antibodies against the virus) when the difference between O.D. against the viral antigen was at least 0.30.

Hereafter there is disclosed a specific test for assaying the above-mentioned disease or exposure to disease risks.

Method.

This ELISA test is for detection and titration of seric anti-retrovirus type LAV antibodies.

It comprises carrying out a competition test between a viral antigen (cultivated on T lymphocytes) and a control antigen constituted by a lysate of the same though non-infected lymphocytes.

The binding of the antibodies on the two antigens is revealed by the use of a human antiglobulin labelled with an enzyme which itself is revealed by the addition of a corresponding substrate.

Preparation of the viral antigen.

The cellular cultures which are used are T lymphocytes of human origin which come from:
umbilical cord blood,
bone marrow,
blood of a healthy donor.

After infection of the cells by the virus, the supernatant of the infected cell culture is used. It is concentrated by precipitating with 10% PEG, then purified (two or three times) on a (20-60%) sucrose gradient by ultracentrifugation to equilibrium.

The viral fractions are gathered and concentrated by centrifugation at 50,000 rotations per minute for 60 minutes.

The sedimented virus is taken up in a minimum volume of buffer NTE at pH 7.4 (Tris 0.01M, NaCl 0.1M, EDTA 0.001M).

The proteic concentration is determined by the Lowry method.

The virus is then lysed by a (RIPA+SDS) buffer (0.5% final) for 15 minutes at 37° C.

Preparation of the control antigen.

The non-infected lymphocytes are cultured according to the preceeding conditions for from 5 to 10 days. They are centrifuged at low speed and lysed in the RIPA buffer in the presence of 5% of the product commercialized under the name of ZYMOFREN (special) (500 u/ml). After a stay of 15 minutes at 4° C. with frequent stirrings with vortex, the lysate is centrifuged at 10,000 rotations per minute. The supernatant constitutes the control antigen. Its concentration in protein is measured by the Lowry method.

Reagents.
1-Plates=NUNC-special controlled ELISA
2-Buffer PBS: pH 7.5
3-TWEEN 20
4-Carbonate buffer: pH=9.6 ($CO_3Na_2$=0.2M) ($CO_3HN_a$=0.2M)
5-Non fetal calf serum: which is stored in frozen state (BIOPRO),
6-Bovine serum albumin (BSA) SIGMA (fraction V)
7-Human anti IgG (H+L) labelled with peroxidase PASTEUR, in tubes of 1 ml preserved at 4° C.
8-Washing buffer=PBS buffer, pH 7.5+0.05% TWEEN 20 Dilution of the conjugate is carried out at the dilution indicated in PBS buffer+TWEEN 20 (0.05%)+bovine albumin 0.5 g per 100 ml.
9-Dilution buffer of sera=PBS buffer+0.05% TWEEN 20+0.5 g BSA bovine serum albumin per 100 ml
10-Substrate=OPD
Citrate buffer pH=5.6 trisodic citrate ($C_6H_5Na_4O_3.2H_2O$), 0.05M; citric acid ($C_6H_8O_7.1H_2O$), 0.05M.
Hydrogen peroxide=at 30% (110 volumes)—used at 0.03% when using citrate buffer.
Orthophenylene diamine=SIGMA 75 mg per 25 ml of buffer—which is diluted in buffer extemporaneously.

Preparation of the plates.

The plates which are used have 96 U-shaped wells (NUNC=ELISA). They include 12 rows of 8 wells each, numbered from 1 to 12.

The distribution of antigens is as follows:
100 yl of the viral antigen, diluted in carbonate buffer at pH 9.6, are deposited in each of the wells of rows (marked)

1-2-5-6-9-10

100 ul of the control antigen, diluted in carbonate buffer at pH 9.6, are deposited in each of the wells of rows (marked)

3-4-7-8-11-12.

The dilution of the viral antigen is titrated at each viral production. Several dilutions of viral antigen are tested and compared to positive and negative known controls (at several dilutions) and to human anti-IgG labelled with peroxidase, the latter being also tested at several dilutions.

As a rule, the proteic concentration of the preparation is from 5 to 2.5 ug/ml.

The same proteic concentration is used for the control antigen.

The plates are closed with a plastic lid and are incubated overnight at 4° C.

Then they are put once in distilled water and centrifuged. The wells are then filled with 300 ul of non-fetal calf serum at 20% in PBS buffer.

The incubation lasts 2 hours at 37° C. (covered plates).

The plates are washed 3 times in PBS buffer with TWEEN 20, 0.05% (PBS-tw buffer):
first washing 300 ul
second and third washing 200 ul/well.

The plates are carefully dried and sealed with an adhesive plastic film. They can be stored at −80° C.

ELISA reaction: antibody titer assay.

After defreezing, the plates are washed 3 times in PBS-TWEEN. They are carefully dried.

The positive and negative control sera as well as the tested sera are diluted first in the tube, with PBS-TWEEN containing 0.5% bovine albumin.

The chosen dilution is 1/40.

100 ul of each serum are deposited in duplicate on the viral antigen and in duplicate on the control antigen. The same is carried out for the positive and negative diluted controls.

The plates equipped with their lids are incubated for 1 h 30 at 37° C.

They are washed 4 times in PBS+TWEEN 0.05%.
100 ul of human anti-IgG (labelled with peroxidase) at the chosen dilution are deposited in each well and incubated at 37° C.

The plates are again washed 5 times with the (PBS+TWEEN) buffer. They are carefully dried.

Revealing the enzymatic reaction is carried out by means of a orthophenylene-diamine substrate (0.05% in citrate buffer pH 5.6 containing 0.03% of $H_2O_2$).

100 ul of substrate are distributed in each well.

The plates are left in a dark room 20 minutes at the laboratory temperature.

Reading is carried out on a spectrophotometer (for microplates) at 492 nm.

Sera deemed as containing antibodies against the virus are those which give an ODD (optical density difference=optical density of viral antigen less optical density of control antigen) equal to or higher than 0.30.

This technique enables a qualitative titration as well as a quantitative one. For this purpose, it is possible either to use several dilutions of the serum to be assayed, or to compare a dilution of the serum with a range of controls tested under the same conditions.

The table hereafter provides first results of serological investigations of LAV antibodies, carried out by using the above exemplified ELISA assay.

LAV virus was labelled with $^{35}$S-cysteine overnight. The supernatant was precipitated with 10 Z PEG 6000 overnight at +4° C. The precipitate was centrifuged 45 minutes at 3,000 rpm and the pellet was redissolved in 400 ul of NTE buffer. The virus suspension was centrifuged in sucrose gradient 20–55 Z in NTE for 120 minutes at 50,000 rpm (SW 55 Ti). Fractions corresponding to the reverse transcriptase peak were pooled, diluted in NTE and the virus centrifuged again at 50,000 rpm for 30 minutes, and resuspended in 200 ul of NTE. It was banded again in a 20–55% sucrose gradient under the same conditions as the first gradient. Aliquots of each fraction were immunoprecipitated with LAV seropositive serum and then electrophoresed on a polyacrylamide (12.5%) gel under denaturing conditions. Another aliquot was tested for reverse transcriptase activity. The autoradiogram shows clearly the association of the viral proteins, including the 110K protein with the viral band.

The experiment shows that LAV purified under the standard conditions used for the ELISA test, described in the British patent application No. 83 24800 and in Science 1983, 220, 868–870, contains the high molecular weight protein, GP110.

TABLE

RESULTS OF SEROLOGICAL INVESTIGATIONS FOR LAV ANTIBODIES

| | Total examined | ELISA-LAV pos-itive | % pos-itive | ELISA-HTLV1+ (Biotech) positive | % positive |
|---|---|---|---|---|---|
| Lymphadenopathy patients* | 35 | 22 | (63) | 5*** | (14) |
| Healthy homosexuals | 40 | 7 | (17) | 1 | (3) |
| Control population | 54 | 1 | (1, 9) | 0 | (2.6) |

*28 homosexuals, 3 Haitians (1 woman), 4 toxicomans (2 women)
+The number of positive sera is probably overestimated in this test, since no control of unspecific binding could be done.
**Out of the 5 LAS HTLV1 positive, 3 were born in Haiti, 1 had stayed for a long time in Haiti and 1 had made several travels to the USA. 11 of them had also antibodies against LAV.

The table shows clearly high prevalence of LAV antibodies in the homosexual patients with LAS, the very low incidence in the normal population and also a moderate spread of virus infection in still healthy homosexuals. In the latter group, all the positive individuals had a high number of partners (50 per year). The incidence of HTLV antibodies was very low in all three groups (determined by using a commercial ELISA test (Biotech)). The groups of AIDS patients gave less interpretable results: approximatively 20% had LAV antibodies, but some of the sera were taken at a very late stage of the disease, with a possible negativation of the humoral response.

It should further be mentioned that lymphocytes of all LAS patients do not produce detectable amounts of LAV-type virus. Particularly, cells of lymph nodes from 6 more LAS patients were put in culture and tested for virus production, as described for patient 1. No virus release could be detected by RT activity. However, a p25 protein recognized by the serum of the first patient could be detected in cytoplasmic extracts of the T-cells labelled with $^{35}$S-methionine in 3 other cases. This suggests partial expression of a similar virus in such cases. Moreover, all (6/6) of these patients had antibodies against LAV p25 proteins, indicating that they all had been infected with a similar or identical virus.

Interestingly, in lymphocytes of one of the patients (patient 2), there was a weak but definite immunoprecipitation of a band of similar size (p24-p25) with goat antiserum raised against HTLV1. Similarly, the patient's serum had antibodies against both HTLV and LAV, suggesting a double infection by either viruses. Such cases seem rather infrequent.

Additional results of LAV serology in French patients.

By using the above-described ELISA test the additional results disclosed hereafter were obtained in the following three groups of persons. The persons of group I appeared indeed as being afflicted with AIDS, LAS or ARC, i.e. AIDS-related complex syndromes. The persons of group II were relatives of the patients of group I who were apparently healthy; results are provided according whether or not they had sexual contacts with patients of group I. The persons of group III were controls unrelated to the persons of the preceding groups.

| | ELISA IgG-LAV positive | Percent positive |
|---|---|---|
| I - AIDS cases | | |
| AIDS | 67/90 | 74.4% |
| LAS, RC | 99/110 | 90% |
| II - Relatives of homosexual AIDS cases | | |
| sexual contacts | 16/34 | 48% |
| non sexual contacts | 0/10 | 0% |
| III - Controls | | |
| gay control group | 14/54 | 26% |
| unselected blood donors | 1/300 | 0.3% |
| laboratory workers | 0/30 | |
| rheumatoid arthritis | 0/30 | |

The results hereabove show a high prevalence of ELISA IgG-LAV positive responses in AIDS, LAS or ARC cases. The data relative to the persons of group II further show that sexual contacts do provide for the transmission of the virus from a sexual partner to another.

The invention finally also relates to the biological reagents that can be formed by the LAV extracts containing the p25 protein or by the purified p25 protein, particularly for the production of antibodies directed against p25 in animals or of monoclonal antibodies. These antibodies are liable of forming useful tools in the further study of antigenic determinants of LAV viruses or LAV-related viruses.

It is acknowledged that the OKT designations are used herein with respect to the designation of some sub-sets of lymphocytes or related monoclonal antibodies for convenience only.

It should further be mentioned that the viral extracts, particularly viral lysates or enriched fractions can also be defined by reference to their immunological relationship or similitude (or similarity) with the extracts or enriched fractions containing a p25 protein or one of the other proteins described above, as obtainable from the strain LAV1, or IDAV2. Thus any protein fraction which is capable of giving similar patterns of immunological reaction as do the protein extracts of LAV1, IDAV1 or IDAV2 with the same sera, must be considered as equivalent thereof and, accordingly, be deemed as encompassed by the scope of the claims which follow. A similar conclusion extends of course to the diagnostic means (process and kits) which may make use of such equivalent protein extracts.

The LAV1 virus has been deposited at the Collection Nationale des Cultures de Micro-organismes (C.N.C.M.), Institute Pasteur, 28 Rue du Docteur Roux, 75724 Paris Cedex 15, under No. I-232 on Jul. 15, 1983 and IDAV1 and IDAV2 viruses have been deposited at the C.N.C.M. on Sep. 15, 1983 under No. I-240 and I-241, respectively. The invention encompasses as well the extracts of mutants or variants of the above deposited strains which possess substantially the same immunological properties.

We claim:

1. An in vitro diagnostic method for the detection of the presence or absence of antibodies which bind to antigens of human retrovirus indicative of Acquired Immune Deficiency Syndrome (AIDS) or of Lymphadenopathy Associated Syndrome (LAS), which method comprises contacting isolated p18 protein of said retrovirus with a biological fluid for a time and under conditions sufficient for the protein and antibodies in the biological fluid to form a complex; and detecting the formation of the complex.

2. The method as claimed in claim 1, wherein the detecting step further comprises measuring the formation of said complex.

3. The method as claimed in claim 1, wherein the biological fluid is human serum.

4. Structural protein of Human Immunodeficiency Virus (HIV), which is p18 protein of said virus, and said protein is in isolated form.

5. A labeled polypeptide, wherein the polypeptide is capable of being immunologically recognized by serum of a patient afflicted with Lymphadenopathy Syndrome (LAS) or Acquired Immune Deficiency Syndrome (AIDS);

the polypeptide is p18 protein of Human Immunodeficiency Virus (HIV) in isolated form; and said label is an immunoassay label selected from the group consisting of a radioactive label, an enzyme label, and a fluorescent label.

6. An in vitro diagnostic method for the detection of the presence or absence of antibodies which bind to antigens of human retrovirus indicative of Acquired Immune Deficiency Syndrome (AIDS) or of Lymphadenopathy Associated Syndrome (pre-AIDS), which method comprises contacting an isolated antigen mixture comprising (A) p18 protein of said retrovirus, and (B) p25 protein of said retrovirus, with a biological fluid, for a time and under conditions sufficient for the antigen and antibody in the biological fluid to form an antigen-antibody complex; and detecting the formation of the complex.

7. An isolated mixture of structural proteins of Human Immunodeficiency Virus (HIV), wherein the proteins are p18 and p25 proteins.

8. An in vitro diagnostic method for the detection of the presence or absence of antibodies which bind to antigens of human retrovirus indicative of Acquired Immune Deficiency Syndrome (AIDS) or of Lymphadenopathy Associated Syndrome (LAS), which method comprises contacting p12 protein of said retrovirus with a biological fluid for a time and under conditions sufficient for the protein and antibodies in the biological fluid to form a complex; and detecting the formation of the complex.

9. Structural protein of Human Immunodeficiency Virus (HIV), which is p12 protein of said virus, and said protein is in isolated form.

10. A labeled polypeptide, wherein the polypeptide is capable of being immunologically recognized by antibodies in the serum of a patient afflicted with Lymphadenopathy Syndrome (LAS) or Acquired Immune Deficiency Syndrome (AIDS);

the polypeptide is p12 protein of Human Immunodeficiency Virus (HIV) in isolated form; and said label is an immunoassay label selected from the group consisting of a radioactive label, an enzyme label, and a fluorescent label.

11. A mixture of structural proteins of Human Immunodeficiency Virus (HIV), wherein the proteins are selected from the group consisting of p12, p18, and p25 proteins, and the mixture is in isolated form.

* * * * *

UNITED STATES PATENT AND TRADEMARK OFFICE
CERTIFICATE OF CORRECTION

PATENT NO. : 5,217,861
DATED : June 8, 1993
INVENTOR(S) : Luc Montagnier et al

It is certified that error appears in the above-indentified patent and that said Letters Patent is hereby corrected as shown below:

On the title page, item [54] lines 2 and 8, and col. 1, lines 3 and 9, in the title change "NAMELY" to read --NAMELY,-- and change "PRE-AIDS" to --PRE-AIDS,--.

On the title page, item [75] Inventors: "Barre-Sinoussi" should be changed to read --Francoise Barre-Sinoussi--.

Signed and Sealed this

First Day of February, 1994

Attest:

BRUCE LEHMAN

*Attesting Officer*    *Commissioner of Patents and Trademarks*

UNITED STATES PATENT AND TRADEMARK OFFICE
CERTIFICATE OF CORRECTION

PATENT NO. : 5,217,861

DATED : June 8, 1993

INVENTOR(S) : Luc Montagnier et al.

It is certified that error appears in the above-identified patent and that said Letters Patent is hereby corrected as shown below:

On the title page, line 3 of the Related U.S. Application Data, change "February 22, 1985" to read --February 28, 1985--.

Signed and Sealed this

Tenth Day of May, 1994

Attest:

BRUCE LEHMAN

Attesting Officer     Commissioner of Patents and Trademarks